(12) United States Patent
Park

(10) Patent No.: US 11,911,071 B2
(45) Date of Patent: Feb. 27, 2024

(54) SMOKE EVACUATION DEVICE WITH FLUID STORAGE FOR LAPAROSCOPIC SURGERY

(71) Applicant: BIO-PROTECH INC., Wonju-si (KR)

(72) Inventor: Ik Ro Park, Irvine, CA (US)

(73) Assignee: BIO-PROTECH INC., Wonju-si (KR)

( * ) Notice: Subject to any disclaimer, the term of this patent is extended or adjusted under 35 U.S.C. 154(b) by 768 days.

(21) Appl. No.: 17/015,983

(22) Filed: Sep. 9, 2020

(65) Prior Publication Data

US 2022/0071658 A1 Mar. 10, 2022

(51) Int. Cl.
*A61B 17/34* (2006.01)
*A61B 17/00* (2006.01)

(52) U.S. Cl.
CPC .... *A61B 17/3423* (2013.01); *A61B 17/00234* (2013.01); *A61B 2217/005* (2013.01); *A61B 2218/008* (2013.01)

(58) Field of Classification Search
CPC ............. A61B 17/3423; A61B 17/00234
USPC ............................................. 606/1
See application file for complete search history.

(56) References Cited

U.S. PATENT DOCUMENTS 8,414,550 B2 * 4/2013 Roberts .............. A61B 17/3474
128/207.14

* cited by examiner

*Primary Examiner* — Nadia A Mahmood
(74) *Attorney, Agent, or Firm* — Studebaker & Brackett PC

(57) ABSTRACT

Proposed is a smoke evacuation device with fluid storage for laparoscopic surgery that can easily filter fluid produced during an operation. According to the smoke evacuation device with fluid storage, water produced in a main body cannot flow back to a filter, so the performance of the filter is not deteriorated and noxious fluid flowing into the main body can be easily filtered out.

18 Claims, 11 Drawing Sheets

SMOKE EVACUATION DEVICE WITH FLUID STORAGE FOR LAPAROSCOPIC SURGERY

BACKGROUND OF THE INVENTION

Field of the Invention

The present invention relates to a smoke evacuation device with fluid storage for laparoscopic surgery and, more particularly, a smoke evacuation device with fluid storage for laparoscopic surgery, the smoke evacuation device with fluid storage being able to keep moisture so that gas produced in the process of laparoscopic surgery can be easily filtered out.

Description of the Related Art

As the optical technology is developed and various laparoscopic devices are rapidly developed, many operations depending on laparotomy in the past have been replaced with laparoscopic surgery. Laparoscopic surgery, which is an operation of minimally opening the stomach of a patient, inserting various surgical instruments including a surgical camera, and performing an operation while observing the inside the abdominal cavity, has an advantage that it causes less complications such as bleeding, infection, adhesion, etc. after an operation, has an effect in terms of beauty because it cuts a small part, and reduces the hospitalization because of less pain and quick recovery after an operation.

According to the procedure of laparoscopic surgery, an operator inserts a needle into a portion around the navel of a patient after the patient is anesthetized, and then injects carbon dioxide into the abdominal cavity to inflate the abdominal cavity. Thereafter, the operator bores a necessary number of port sites at appropriate positions. The operator inserts a camera through a laparoscopic trocar, whereby the image of the inside of the abdominal cavity is shown through a monitor provided in front of the operator and the operator performs a desired operation using appropriately surgical instruments while looking at the monitor.

Meanwhile, when operating devices such as a laser, an electrosurgical unit, an ultrasonic cutting machine in laparoscopic surgery, a lot of noxious gas is produced during the operation. Such gas obstructs the view of an operator and is malodorous, and may contain chemical and pathological noxious particles such as carbon oxide, carbon dioxide, bacteria, and virus. Accordingly, a gas filter apparatus for removing such gas is disposed in the exhaust tube of laparoscopic trocars to secure safety of an operator against such gas. However, since moisture is contained in the gas that is discharged to the gas filter apparatus, the moisture condenses due to the temperature difference between the inside and the outside of the body when the gas is discharged out of the body. When the water permeates into the gas filter apparatus, the performance of the filter is deteriorated.

SUMMARY OF THE INVENTION

In order to solve the problems in the related art, an objective of the present invention is to provide a smoke evacuation device with fluid storage for laparoscopic surgery, the smoke evacuation device with fluid storage being able to keep moisture so that gas produced in the process of laparoscopic surgery can be filtered out.

In order to achieve the objectives of the present invention, a smoke evacuation device with fluid storage for laparoscopic surgery, which is coupled to an exhaust part of a laparoscopic trocar that is inserted into a human body in laparoscopic surgery, includes: a main body having an empty space and having an intake port formed through a first side thereof to be connected with the exhaust part and a discharge port formed through a second side; and a filter disposed at a first side in the main body, in which a first guide pipe through which fluid flowing into the intake port flows to a second side in the main body and a second guide pipe formed along an outer surface of the first guide pipe are disposed in the main body, and when fluid is guided into the main body by the first guide pipe, moisture in the fluid is kept in the main body and gas in the fluid moves toward the filter through a space between the first guide pipe and the second guide pipe, is filtered out, and is then discharged through the discharge port.

The space in the main body may include a first space that communicates with the intake port, a second space that is disposed at a first side of the first space to communicate with the discharge port and in which the filter is disposed, a third space that is positioned between a second side of the first space and the second space, a second guide hole may be formed at the first side of the first space toward the second space, and a first guide hole may be formed at the second side of the first space toward the third space; the first guide pipe may have a first side connected to the intake port and a second side extending through the first guide hole to be positioned in the third space and has a diameter smaller than the first guide hole; and the second guide pipe may have a first side connected to an inner edge of the first guide hole and a second side extending along the outer surface of the first guide pipe to be positioned in the third space.

A first partition may be formed between the first side of the first space and the second space, a second partition may be formed between the second space and the third space, and a third partition may be formed between the third space and the first space; the second guide hole may be formed through the first partition wall and the first guide hole is formed through the third partition; and fluid guided into the third space through the intake port and the first guide pipe from the exhaust part of the laparoscopic trocar may move through a space between the first guide pipe and the second guide pipe and then may be guided into the first space through the first guide pipe, the fluid guided into the first space may move into the second space through the second guide hole, and gas of the fluid guided into the second space may be filtered out by the filter disposed in the second space and then discharged through the discharge port.

The second guide pipe may have: a funnel portion has: a funnel portion connected to the inner edge of the first guide hole and protruding from the first guide hole such that a width thereof decreases as it goes away from the first guide hole; and an outer extension extending from an end of the funnel portion toward an end of the second guide pipe.

An end of the first guide pipe may protrude further than an end of the second guide pipe.

An end of the first guide pipe and an end of the second guide pipe may not be in contact with an inner side of the third space.

The first guide pipe and the second guide pipe may be spaced apart from a bottom side, which faces the ground, of the inner side of the third space.

The first guide pipe and the second guide pipe may be in parallel with the bottom side.

The intake port may be disposed higher than the first guide hole, and the first guide pipe may have an inclined portion having a first side connected to the intake port and a second side inclined downward toward the first guide hole, and an inner extension extending from the second side of the inclined portion and spaced apart from the bottom side.

A diameter of the inclined portion may increase from the first side thereof positioned at the intake port to the second side thereof positioned at the first guide hole.

The smoke evacuation device with fluid storage may further include a door member adjusting an opening area of the discharge port.

An edge part may protrude outward from the main body along an inner edge of the discharge part; an inner edge of the edge part may have a first inner edge, a second inner edge, and a third inner edge sequentially positioned away from the second space; a blocking portion may be formed to close a first side of the first inner edge and an opening portion may be formed to open a second side of the first edge; a pair of guide rails may be formed at both sides in a longitudinal direction of the second inner edge, the blocking portion may be positioned between first sides of the pair of guide rails, and the opening portion may be positioned between second sides of the pair or guide rails; a cover portion may be formed to cover the third inner edge, a slit may be formed in a longitudinal direction of the cover portion, a first side of the slit may be positioned to face the blocking portion, and a second side of the slit may be positioned to face the opening portion; a first side of the door member may have an area being able to close the opening portion and may slide along the guide rails, and a second side of the door member may protrude out of the edge part through the slit; and when the second side of the door member slides along the slit, the first side of the door member may adjust an opening area of the opening portion while moving along the guide rail.

A cover plate may be formed to cover an inner edge of the discharge port; a through-hole may be formed through a first side, which faces the blocking portion, of the cover plate; the first side of the cover plate which faces the blocking portion may be positioned away from the second guide hole further than a second side of the cover plate; and a first side of the filter may be positioned to cover the second guide hole and a second side of the filter may be positioned to face the through-hole.

The intake port and the first guide hole may be positioned to face each other and the first guide hole may have a larger diameter than the intake port.

The second space may include a first internal space that communicates with the second guide hole, a second internal space that communicates with the discharge port, and a third internal space that is positioned between the first internal space and the second internal space, in which a first internal partition may be formed between the first internal space and the second internal space, a second internal partition may be formed between the second internal space and the third internal space, and a third internal partition may be formed between the second internal space and the first internal space; a first internal hole may be formed through the third internal partition and a second internal hole may be formed through the second internal partition; the filter may be disposed in the first internal space; the smoke evacuation device with fluid storage may further include a door member adjusting an opening area of the first internal hole; and gas of fluid moving into the first internal space through the second guide hole may be filtered out by the filter and then may move into the third internal space through the first internal hole, the gas moving into the third internal space may move into the second internal space through the second internal hole, and the gas moving into the second internal space may be discharged to the discharge port.

The door member may have: a rotary shaft mounted on a first side of the third internal partition, a rotary plate formed in a plate shape to cover the first internal hole, having the rotary shaft inserted in a center thereof, and having an opening hole at a first side, and a knob having a first side connected to the rotary shaft and a second side disposed outside the main body through the main body; and the opening hole may be moved to face or not to face the first internal hole by rotation of the knob, whereby the first internal hole may be opened or closed.

The opening hole may be formed in an arch shape along a rotational circumference of the rotary plate such that a width increases from a first side to a second side; and a size opened to the outside of the first internal hole when the first side of the opening hole is positioned to face the first internal hole may be larger than a size opened to the outside of the first internal hole when the second side of the opening hole is positioned to face the first internal hole.

The discharge port may be positioned at an upper portion of the main body and the intake port may be positioned lower than the discharge port, so gas guided into the main body through the intake port may be manually discharged to the discharge port.

Gas discharged to the discharge portion from the inside of the main body may be automatically discharged by a suction device disposed at the discharge port and suctioning gas.

According to the present invention, water produced in the third space cannot flow back into the second guide plate due to condensation of fluid flowing into the third space, so the performance of the filter is not deteriorated and the filter can easily filter gas flowing into the main body.

Further, since the end of the inner extension protrudes further than the end of the outer extension, water of fluid dropping into the third space from the inner extension does not flow back into the outer extension.

Further, since the funnel portion increases in diameter as it goes away from the outer extension, gas guided into the funnel portion through the outer extension is guided into the first space without a bottleneck.

Further, since the cover plate supports a side of the filter, the filter can be formed large regardless of the size of the discharge port.

Further, since the first guide pipe is inclined downward, moisture contained in fluid flowing inside through the intake port easily flows down to the inner extension along the inclined portion.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Hereafter, the smoke evacuation device with fluid storage for laparoscopic surgery according to exemplary embodiments of the present invention are described in detail with reference to the accompanying drawings.

Figure 1:
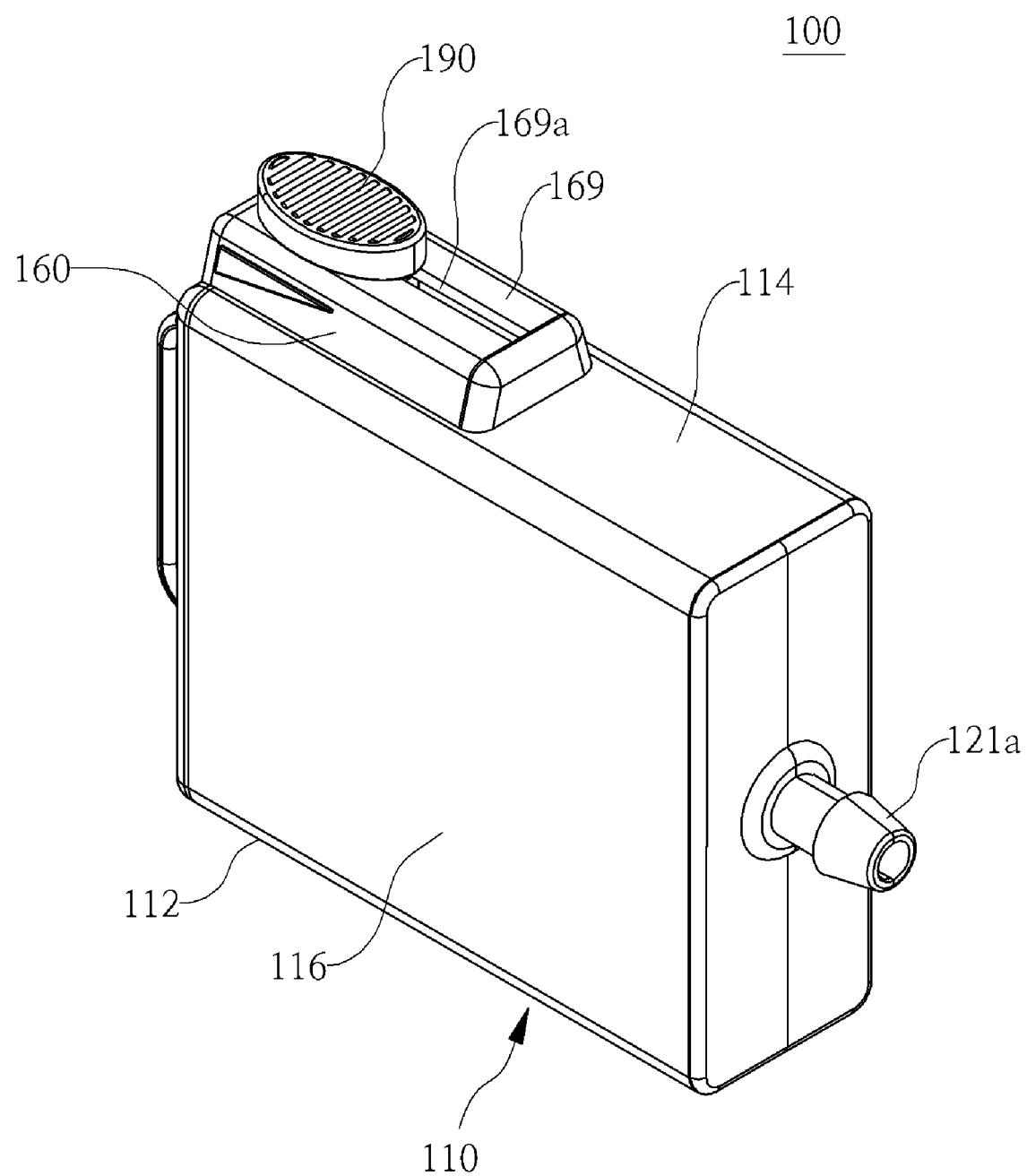
FIG. 1 is a view schematically showing the front of a smoke evacuation device with fluid storage for laparoscopic surgery according to a first embodiment of the present invention.
Figure 2:
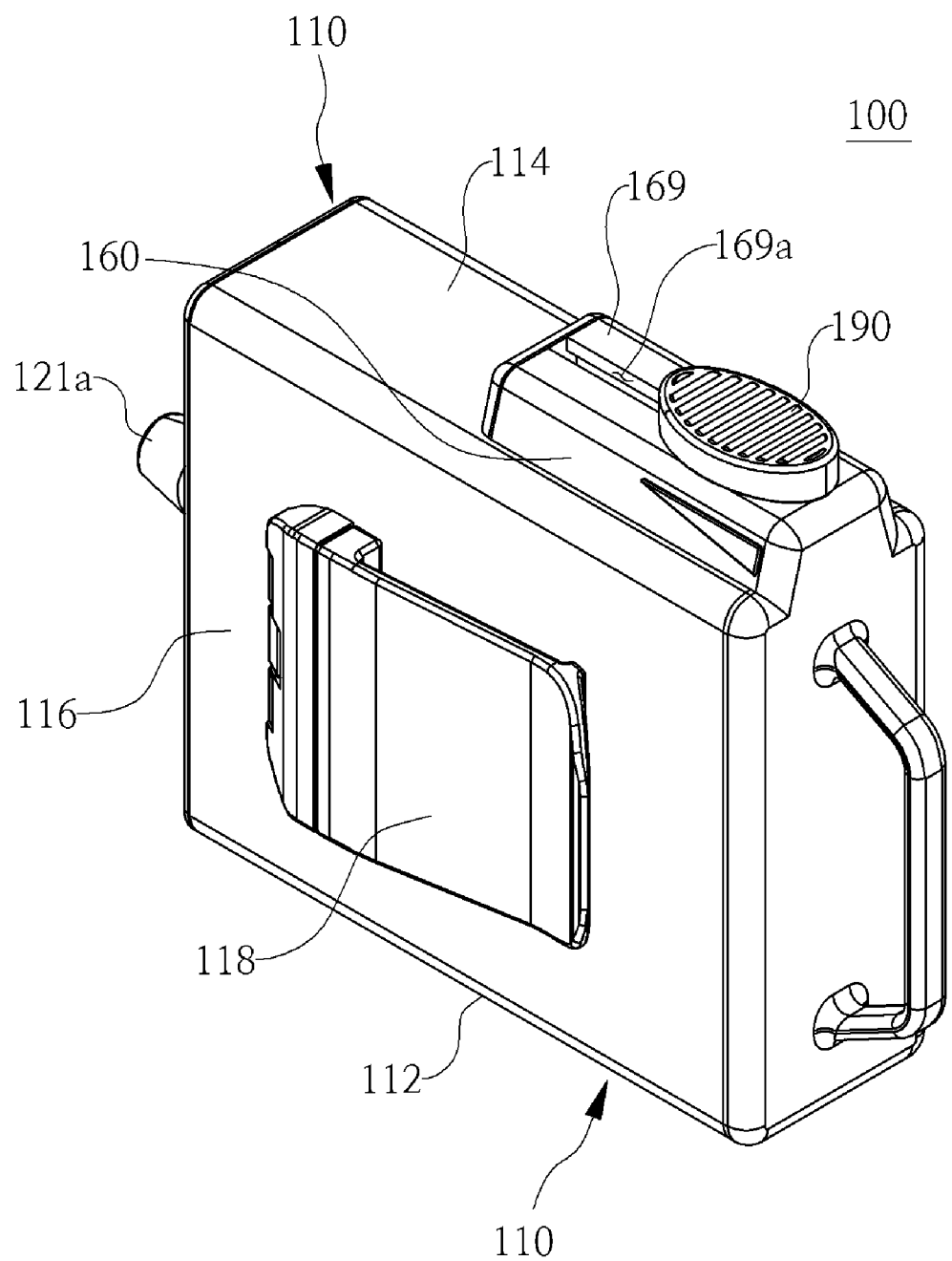
FIG. 2 is a view schematically showing the rear of the smoke evacuation device with fluid storage for laparoscopic surgery according to the first embodiment of the present invention.

FIG. 1 is a view schematically showing the front of a smoke evacuation device with fluid storage for laparoscopic surgery according to a first embodiment of the present invention and FIG. 2 is a view schematically showing the rear of the smoke evacuation device with fluid storage for laparoscopic surgery according to the first embodiment of the present invention.

Referring to FIGS. 1 and 2, a smoke evacuation device with fluid storage 100 for laparoscopic surgery according to a first embodiment of the present invention is, for example, coupled to an exhaust part (not shown) of a laparoscopic trocar that is inserted into a human body to filter various gases receiving from the exhaust part of the laparoscopic trocar, and includes a main body 10, a filter 180 (shown in FIG. 3), and a door member 190.

The main body 110 has an empty space therein and is formed in a substantially hexahedral shape. The main body 110 has a top 114, a bottom 112 spaced down apart from the top 114, and a side wall 116 integrally connecting the top 114 and the bottom 112. An intake port 112 that is connected to an exhaust part is formed though a first side of the side wall 116 and a connecting protrusion 121a is formed at the intake port 121 for easy connection to the exhaust part. A coupling portion 118 for fastening the main body 110 at a specific position in an operating room, etc. is disposed on a second side of the side wall 116. A discharge port 123 (shown in FIG. 3) for discharging gas flowing in the main body 110 from the exhaust part of a laparoscopic trocar is formed through the top 114. An edge part 160 is formed along the inner edge of the discharge port 123 and protrudes outward from the main body 110. A cover portion 169 is formed to cover the edge part 160 and a slit 169a is formed in the longitudinal direction of the cover portion 169. The door member 190 adjusts the opening area of the discharge port 123 by sliding in the slit 169a.

Figure 3:
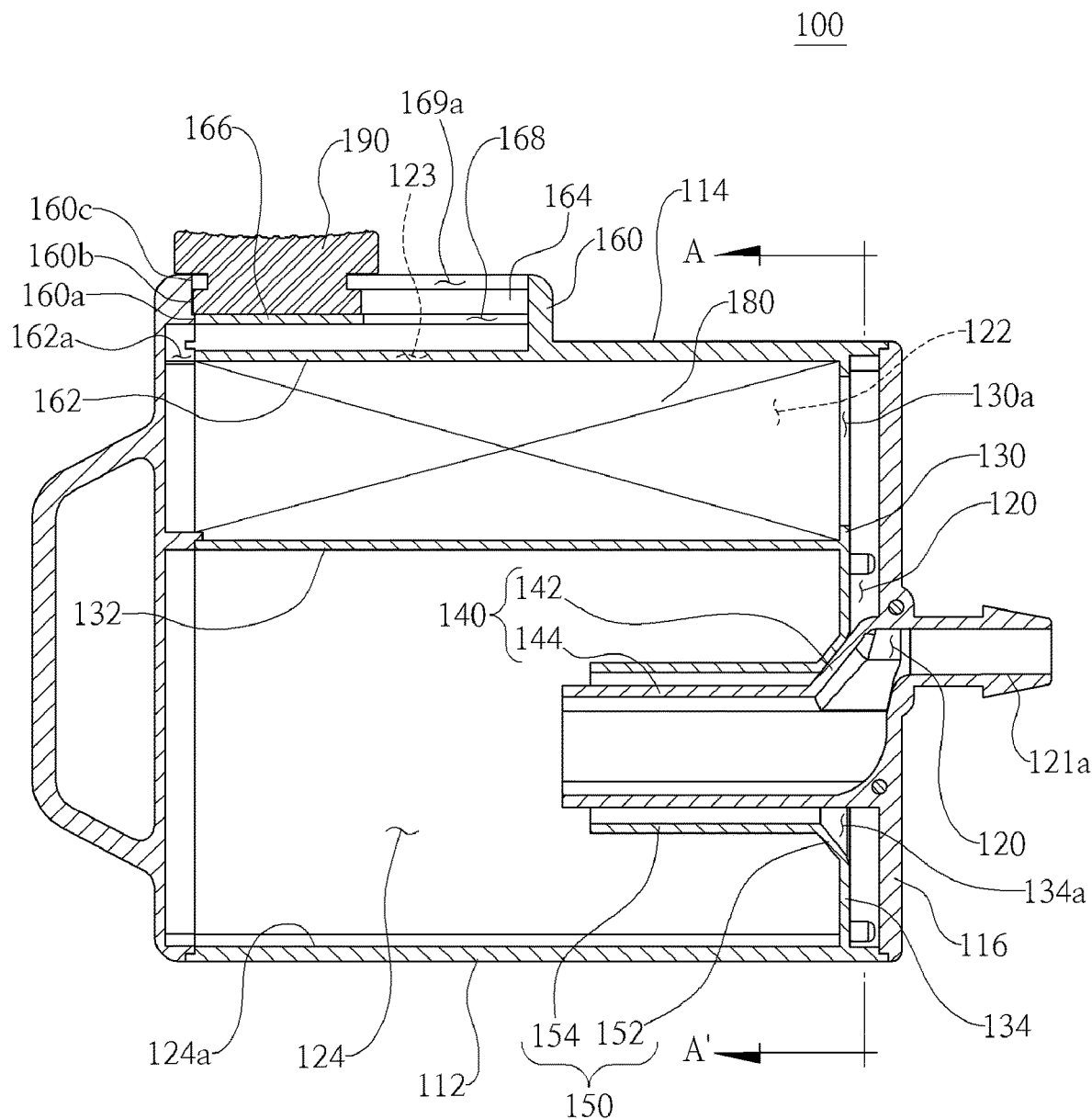
FIG. 3 is a view schematically showing the inside of the main body of the smoke evacuation device with fluid storage for laparoscopic surgery according to the first embodiment of the present invention.
Figure 4:
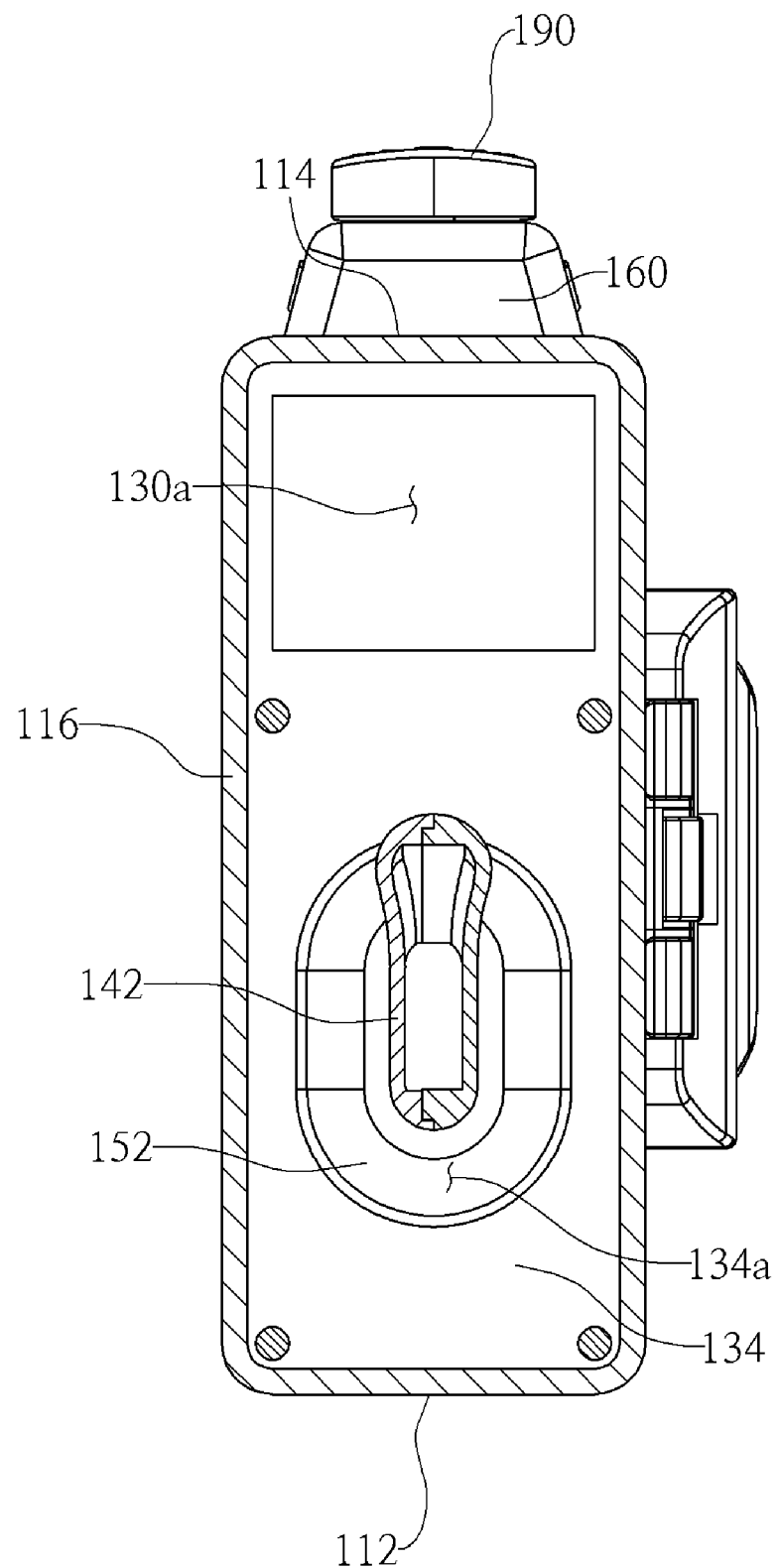
FIG. 4 is a view showing an A-A' cross-section of FIG. 3.

FIG. 3 is a view schematically showing the inside of the main body of the smoke evacuation device with fluid storage for laparoscopic surgery according to the first embodiment of the present invention and FIG. 4 is a view showing an A-A' cross-section of FIG. 3.

Referring to FIGS. 1 to 4, the internal space of the main body 110 includes a first space 120 that communicates with the intake port 121, a second space 122 that communicates with the discharge port 123 and in which a filter 180 is disposed, and a third space 124 that is positioned between the first space 120 and the second space 122. The first, second, and third spaces 120, 122, and 124 are independently separated, and to this end, a first partition 130 is formed between the first space 120 and the second space 122, a second partition 132 is formed between the second space 122 and the third space 124, and a third partition 134 is formed between the third space 124 and the first space 120. A second guide hole 130a is formed through the first partition 130 and a first guide hole 134a is formed through the third partition 134. The intake port 121 has a first guide pipe 140 and a second guide pipe 150 is formed at the first guide hole 134a.

A first side of the first guide pipe 140 is connected to the inner edge of the intake port 121 and a second side thereof is extended and positioned in the third space 124 through the first guide hole 134a. The first guide pipe 140 is smaller in diameter than the first guide hole 134a. The intake portion 121 is positioned higher than the first guide hole 134a, so the first guide pipe 140 has an inclined portion 142 having a first side connected to the intake port 121 and a second side inclined downward to the first guide hole 134a, and an inner extension 144 extending from the second side of the inclined portion 142 and spaced apart from the bottom 112. Since the first guide pipe 140 is inclined downward, moisture contained in the fluid flowing inside through the intake port easily flows into the inner extension 144 through the inclined portion 142. The diameter of the inclined portion 142 increases toward the second side thereof disposed in the first guide hole 134a from the first side thereof positioned in the intake port 121. Since the inclined portion 142 gradually increases in diameter, gas and moisture easily flow from the inclined portion 142 to the inner extension 144 without a bottleneck.

The second guide pipe 150 has a first side connected to the inner edge of the first guide hole 134a and a second side extended along the outer surface of the first guide pipe 140 and positioned in the third space 124. The second guide pipe 150 is larger in diameter than the first guide pipe 140 such that the first guide pipe 140 is positioned inside the second guide pipe 150. The second guide pipe 150 has a funnel portion 152 connected to the inner edge of the first guide hole 134a and protruding from the first guide hole 134a in a cone shape of which the width decreases as it goes away from the first guide hole 134a, and an outer extension 154 extending from the end of the funnel portion 152 to the end of the second guide pipe 150.

Gas guided from the exhaust part of a laparoscopic trocar into the third space 124 through the intake port 121 and the first guide pipe 140 moves through the space between the first guide pipe 140 and the second guide pipe 150 and is then guided into the first space 120 through the first guide hole 134a. The end of the inner extension 144 protrudes further than the end of the outer extension 154, so there is an effect that moisture dropping into the third space 124 through the inner extension 144 does not flow back into the outer extension 154. Since the water produced in the third space 124 cannot flow back into the second guide pipe 150, the performance of the filter 180 is not influenced by the water in the third space 124, so there is an effect that the filter 180 can easily filter the gas flowing in the main body 110. Since the funnel portion 152 increases in diameter as it goes away from the outer extension 154, there is an effect that gas that is guided to the funnel portion 152 through the outer extension 154 is easily guided into the first space 120 without a bottleneck.

The end of the first guide pipe 140 and the end of the second guide pipe 150 are not in contact with the inner side of the third space 124. Accordingly, there is an effect in terms of structure that the moisture dropping into the third space 124 cannot flow back into the end of the first guide pipe 140 or the end of the second guide pipe 150. Further, according to the present invention, the first guide pipe 140 and the second guide pipe 150 may be spaced apart from the bottom side 124a, which faces the ground, of the inner side of the third space 124. The first guide pipe 140 and the second guide pipe 150 may be in parallel with the bottom side 124a. Accordingly, there is an effect foreign substances such as water dropping down to the bottom side 124a through the first guide pipe 140 and accumulated in the third space 124 cannot flow back into the second guide pipe 150.

The third space 124 has a large volume to be able to keep a sufficient amount of water. However, since the first space 120 connects the third space 124 and the second space 122, the first space 120 may be smaller than the second space 122 and the third space 124.

Figure 5:
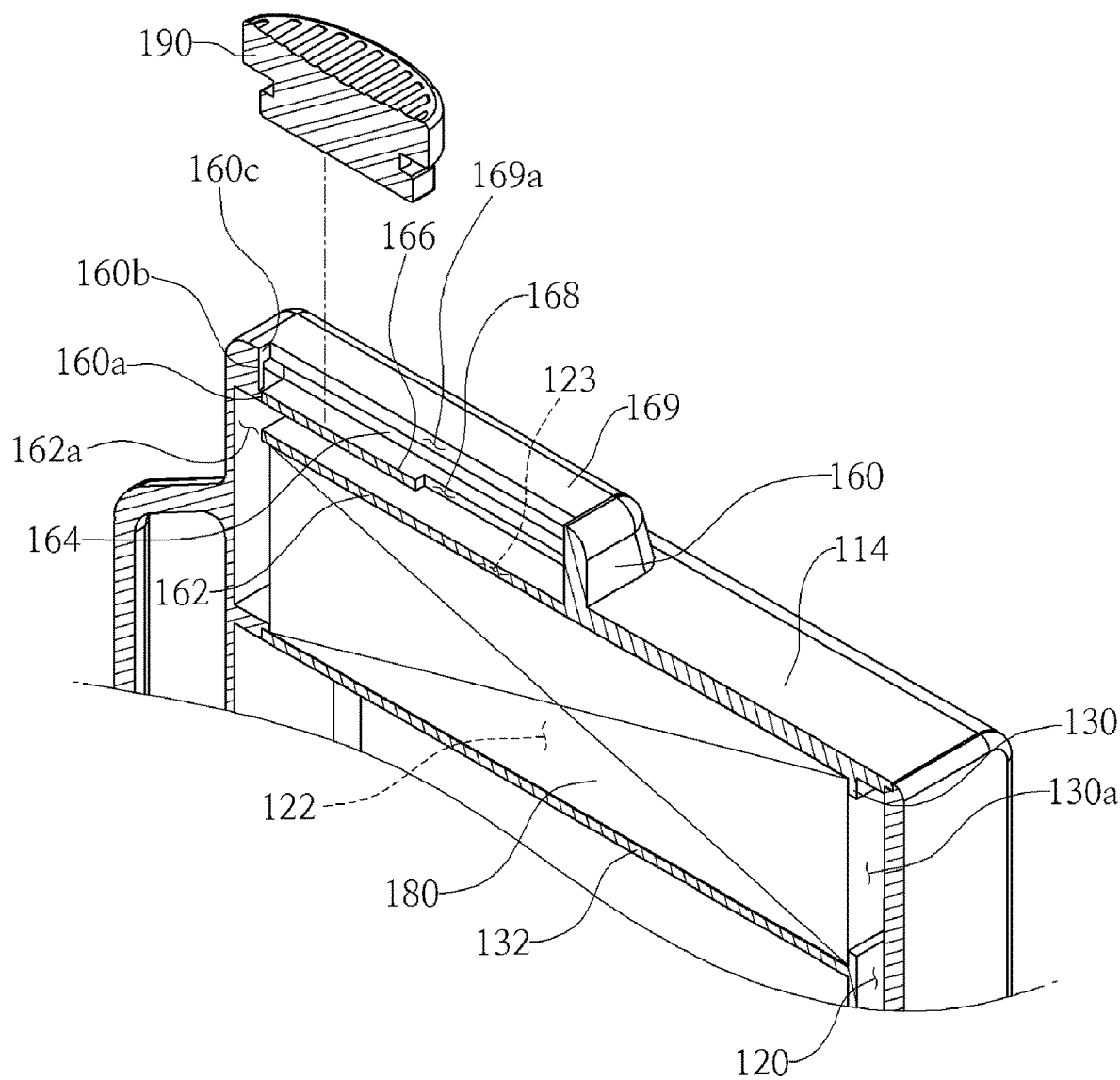
FIG. 5 is a view schematically showing the state in which a door member is coupled to an edge part in the smoke evacuation device with fluid storage for laparoscopic surgery according to the first embodiment of the present invention.

FIG. 5 is a view schematically showing the state in which a door member is coupled to an edge part in the smoke evacuation device with fluid storage for laparoscopic surgery according to the first embodiment of the present invention.

Referring to FIGS. 1 to 5, the filter 180 is disposed in the second space 122. Gas guided into the first space 120 moves into the second space 122 through the second guide hole 130a. The gas guided into the second space 122 is filtered out by the filter 180 disposed in the second space 122 and then discharged through the discharge port 123. The door member 190 is coupled to the edge part 160 to adjust the opening area of the discharge port 123.

The inner edge of the edge part 160 has a first inner edge 160a, a second inner edge 160b, and a third inner edge 160c that are positioned sequentially away from the second space 122. A blocking portion 166 is formed to close a first side of the first inner edge 160a and an opening portion 168 is formed to open a second side of the first inner edge 160a. A pair of recessed guide rails 163 is formed at both sides in the longitudinal direction of the second inner edge 160b, the blocking portion 166 is positioned between first sides of the pair of guide rails 164, and the opening portion 168 is positioned between second sides of the pair or guide rails 164. A cover portion 169 is formed to close the third inner edge 160c, a slit 169a is formed in the longitudinal direction of the cover portion 169 and has a first side facing the blocking portion 166 and a second side facing the opening portion 168.

A first side of the door member 190 has an area being able to close the opening portion 168 and can slide in the guide rails 164 and a second side of the door member 190 protrudes out of the edge part 160 through the slit 169a. When a user holds and slides the second side of the door member 190 along the slit 169a, the first side of the door member 190 moves along the guide rails 164, whereby the opening area of the opening portion 168 is adjusted. That is, when the first side of the door member 190 is positioned to face the opening portion 168, the opening portion 168 is closed, so gas discharged through the discharge port 123 cannot be discharged out of the second space 122. On the contrary, when the first side of the door member 190 is moved to the blocking portion 166 and the opening portion 168 is opened to the slit 169a, the gas discharged through the discharge port 123 is discharged out of the second space 122.

The size of the filter 180 disposed in the second space 122 may be limited, depending on the size of the discharge port 123. That is, gas flows into the filter 180 through a longitudinal first end of the filter 180 and the gas flowing in the filter 180 is filtered out while moving through the filter 180 and is then discharged through a second end of the filter 180. Accordingly, the discharge port 123 should be positioned close to the second end of the filter 180. However, according to the present invention, the door member 190 can move over the discharge port 123, the size of the discharge port 123 should be as large as the movable displacement of the door member 190. This acts as a reason that limits the size of the filter 180.

In order to solve the problem in the present invention, a cover plate 162 is formed to cover the inner edge of the discharge port 123, a through-hole 162a is formed through a first side, which faces the blocking portion 166, of the cover plate 162. Further, the first side of the cover plate 162 which faces the through-hole 162a is positioned away from the second guide hole 130a further than a second side of the cover plate 162. A first end of the filter 180 is positioned to cover the second guide hole 130a and a second end of the filter 180 is positioned to face the through-hole 162a. Since a side of the filter 180 is supported by the cover plate 162, there is an effect that the filter 180 can be formed large regardless of the size of the discharge port 123.

Hereafter, the operation of the smoke evacuation device with fluid storage for laparoscopic surgery according to the first embodiment of the present invention is described.

Figure 6:
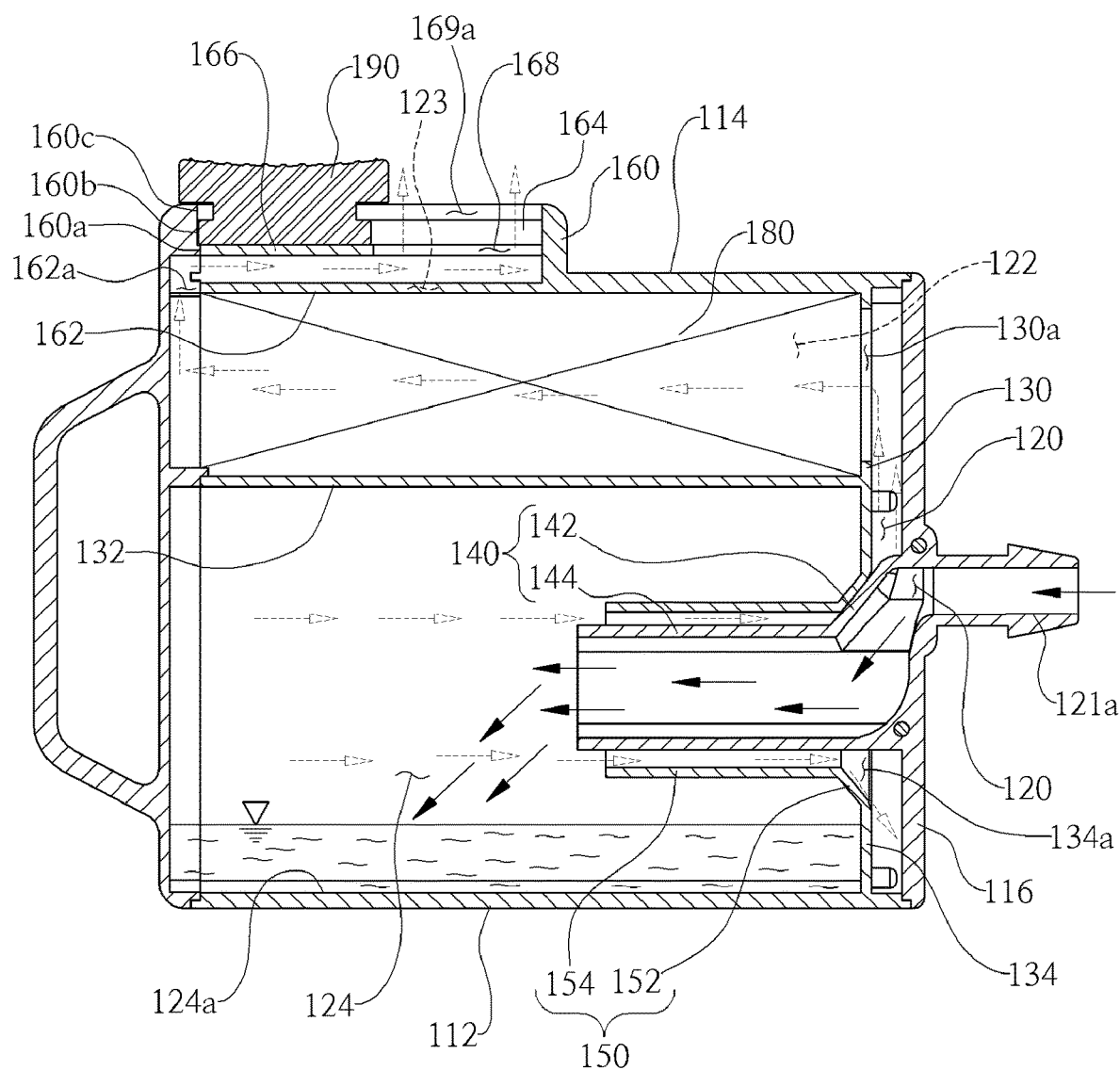
FIG. 6 is a view schematically showing the flowing path of fluid that flows into the smoke evacuation device with fluid storage for laparoscopic surgery according to the first embodiment of the present invention.

FIG. 6 is a view schematically showing the flowing path of fluid that flows into the smoke evacuation device with fluid storage for laparoscopic surgery according to the first embodiment of the present invention.

Referring to FIGS. 1 to 6, the exhaust part (not shown) of a laparoscopic trocar and the connecting protrusion 121a are connected to each other by a connecting tube (not shown). In this state, a user slides the door member 190 to the blocking portion 166 to open the opening portion 168. Accordingly, fluid flowing into the intake port 121 through the connecting protrusion 121a is guided into the third space 124 through the first guide pipe 140. Moisture contained in the fluid and water produced by condensation due to a temperature difference are kept in the third space 124. Gas moving into the third space 124 moves through the space between the first guide pipe 140 and the second guide pipe 150 and is then guided into the first space 120 through the first guide hole 134a. The gas guided into the first space 120 moves into the second space 122 through the second guide hole 130a. The gas guided into the second space 122 is filtered out by the filter 180 disposed in the second space 122 and then discharged outside sequentially through the through-hole 162a and the opening portion 168.

As described above, since the water produced in the third space 124 due to condensation of the fluid flowing in the third space 124 cannot flow back into the second guide pipe 150, the performance of the filter 180 is not deteriorated, so the filter 180 can easily filter the gas flowing in the main body 110.

Figure 7:
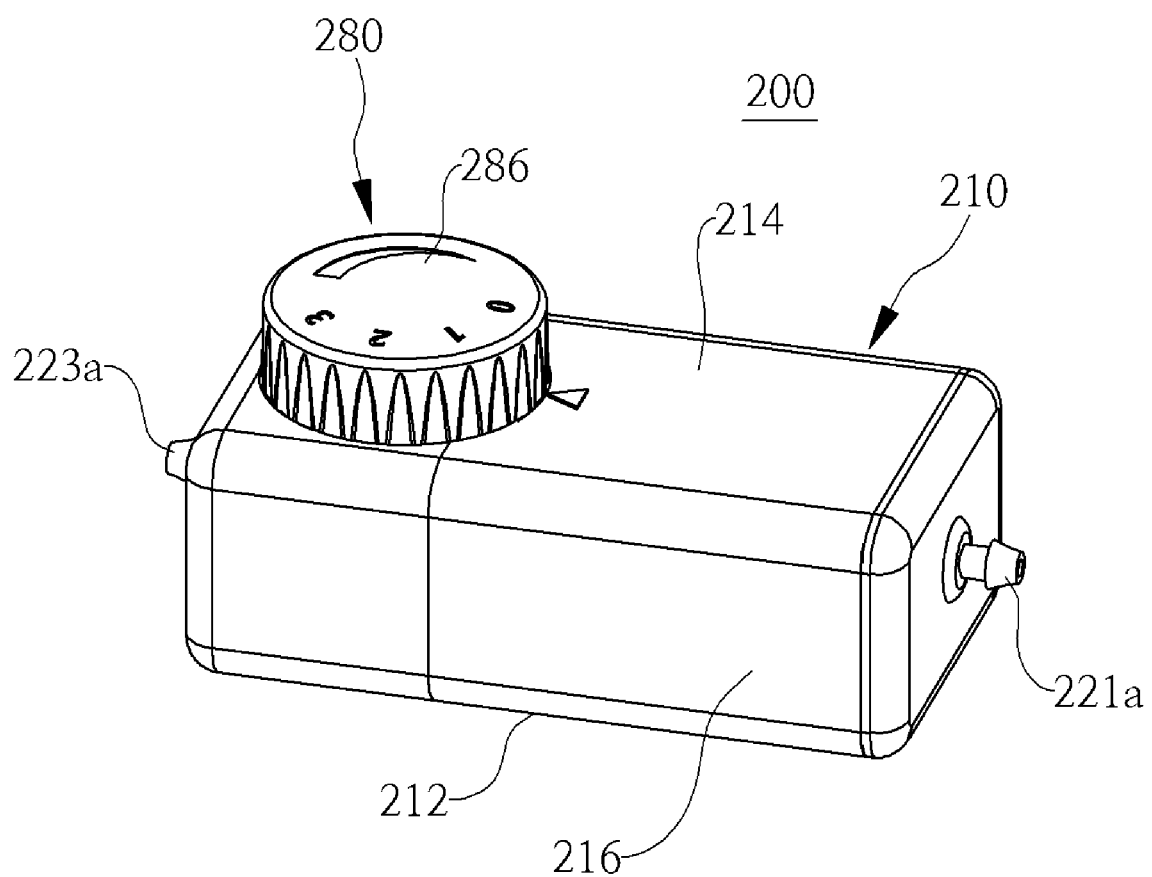
FIG. 7 is a view schematically showing a smoke evacuation device with fluid storage for laparoscopic surgery according to a second embodiment of the present invention.

FIG. 7 is a view schematically showing a smoke evacuation device with fluid storage for laparoscopic surgery according to a second embodiment of the present invention.

Referring to FIG. 7, a smoke evacuation device with fluid storage 200 for laparoscopic surgery according to a second embodiment of the present invention includes a main body 210, a filter 260 (shown in FIG. 8), and a door member 280.

The main body 210 has an empty space therein and has a top 214, a bottom 212 spaced down apart from the top 214, and a side wall 216 integrally connecting the top 214 and the bottom 212. An intake port 221 for connection with an exhaust part (not shown) of a laparoscopic trocar is formed through a first side of the side wall 216 and a connecting protrusion 221a is formed at the intake port 221. A discharge port 223 for discharging gas flowing in the main body 210 to the outside is formed through a second side of the side wall 216. The door member 280 is rotatably disposed on the top 214 and the amount of gas that is discharged out of the main body 210 depends on the rotation angle of the door member 280.

Figure 8:
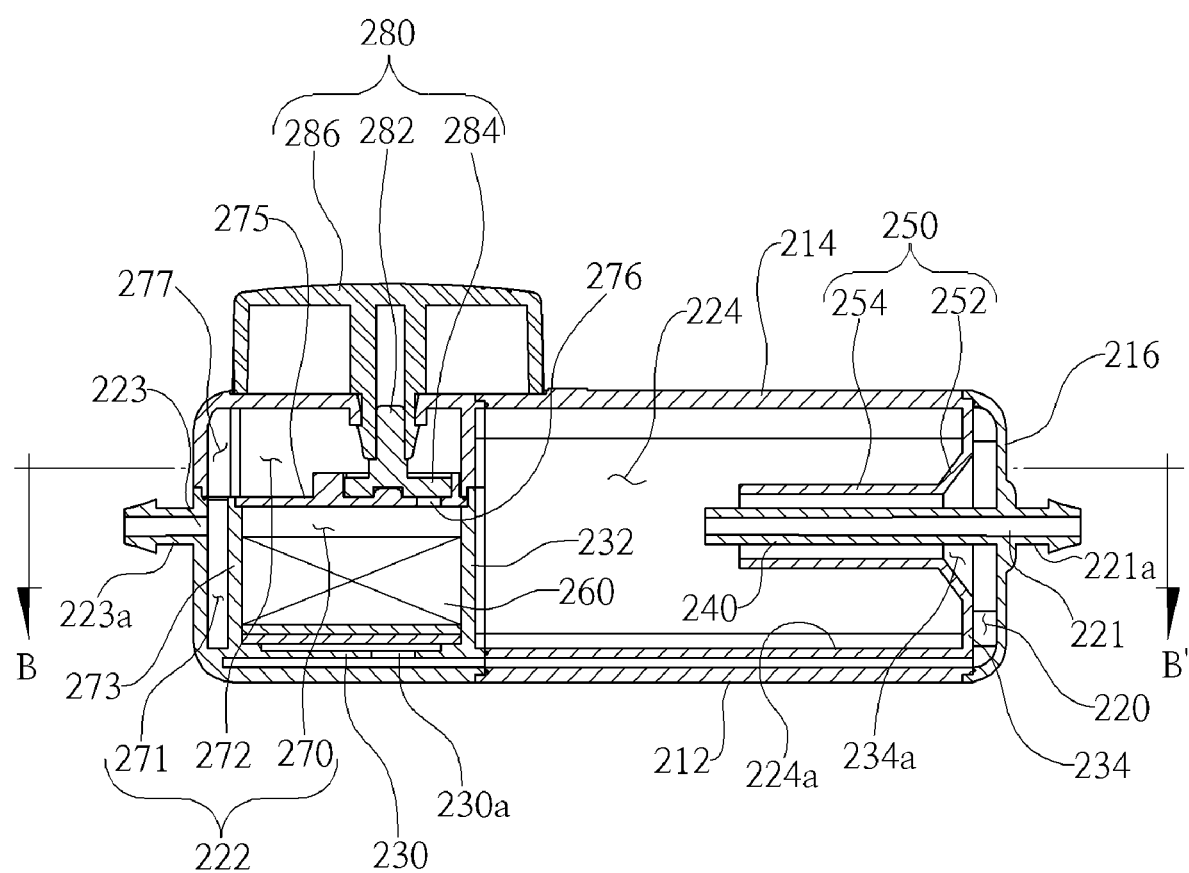
FIG. 8 is a view schematically showing a cross-section of the smoke evacuation device with fluid storage for laparoscopic surgery according to the second embodiment of the present invention.

FIG. 8 is a view schematically showing a cross-section of the smoke evacuation device with fluid storage for laparoscopic surgery according to the second embodiment of the present invention.

Referring to FIGS. 7 to 8, the internal space of the main body 210 includes a first space 220 that communicates with the intake port 221, a second space that communicates with the discharge port 223 and in which the filter 260 is disposed, and a third space 224 that is positioned between the first space 220 and the second space 222. The first, second, and third spaces 220, 222, and 224 are independently separated, and to this end, a first partition 230 is formed between the first space 220 and the second space 222, a second partition 232 is formed between the second space 222 and the third space 224, and a third partition 234 is formed between the third space 224 and the first space 220. A second guide hole 230a is formed through the first partition 230 and a first guide hole 234a is formed through the third partition 234. The first guide hole 232a and the intake port 221 face each other. The first guide hole 234a has a diameter larger than the intake port 221. The intake port 221 has a first guide pipe 240 and a second guide pipe 250 is formed at the first guide hole 234a.

A first side of the first guide pipe 240 is connected to the inner edge of the intake port 221 and a second side thereof is extended and positioned in the third space 224 through the first guide hole 234a. The first guide pipe 240 is smaller in diameter than the first guide hole 234a.

The second guide pipe 250 has a first side connected to the inner edge of the first guide hole 234a and a second side extended along the outer surface of the first guide pipe 240 and positioned in the third space 224. The second guide pipe 250 is larger in diameter than the first guide pipe 240 such that the first guide pipe 240 is positioned inside the second guide pipe 250.

Gas guided from the exhaust part of a laparoscopic trocar into the third space 224 through the intake port 221 and the first guide pipe 240 moves through the space between the first guide pipe 240 and the second guide pipe 250 and is then guided into the first space 220 through the first guide hole 234a.

The end of the first guide pipe 240 and the end of the second guide pipe 250 are not in contact with the inner side of the third space 224. The longitudinal sides of the first guide pipe 240 and the second guide pipe 250 are spaced apart from a bottom side 224a of the third space 224 in parallel with the bottom side 224a, so there is an effect that foreign substances such as water dropping to the bottom side 224a from the first guide pipe 240 and kept in the third space 224 cannot flow back into the second guide pipe 250.

Figure 9:
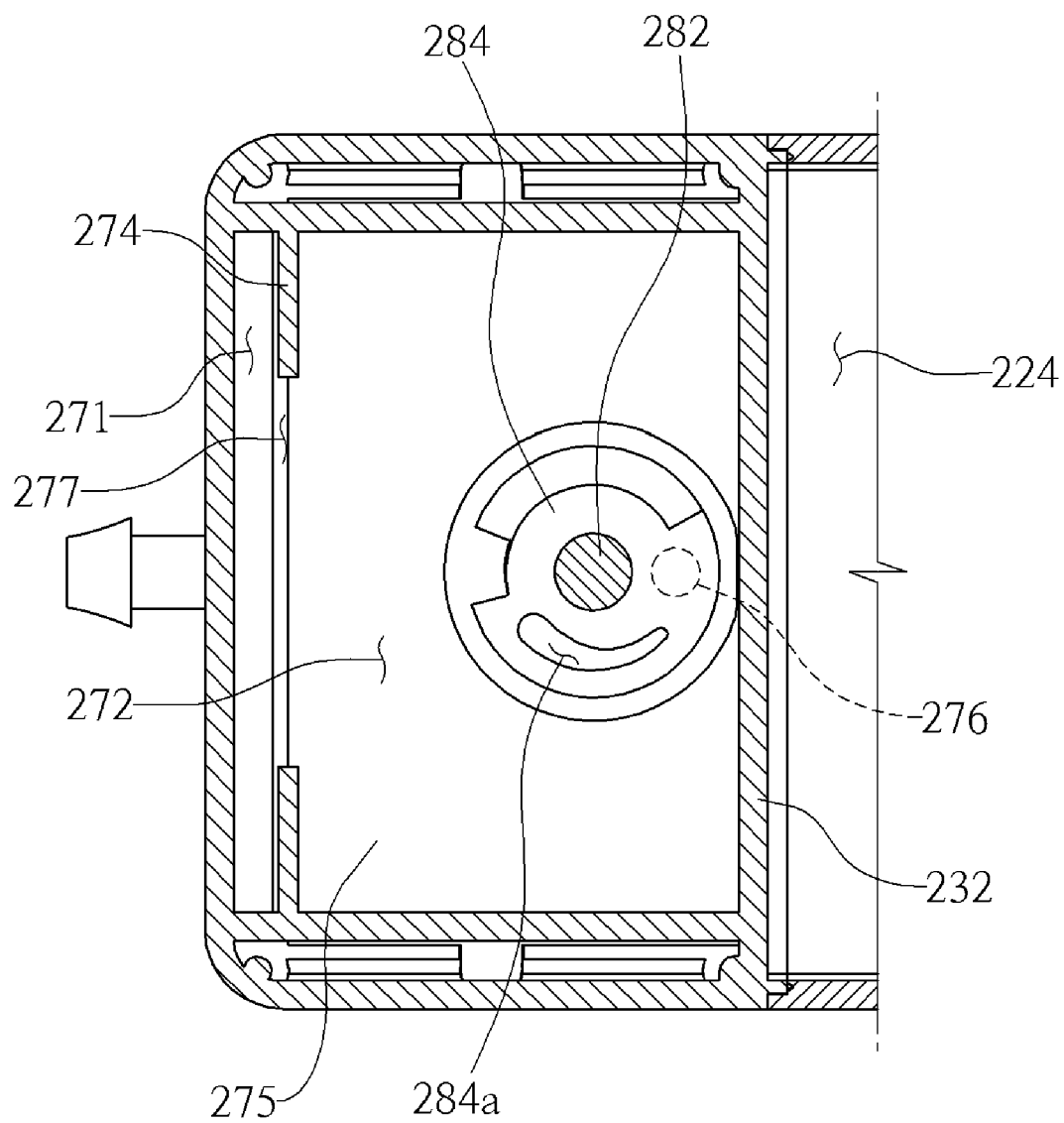
FIG. 9 is a cross-sectional view schematically showing an B-B' cross-section of FIG. 8.

FIG. 9 is a cross-sectional view schematically showing a B-B' cross-section of FIG. 8.

Referring to FIGS. 7 to 9, the second space 222 includes a first internal space 270 that communicates with the second guide hole 230a, a second internal space 271 that communicates with the discharge port 223, and a third internal space 272 that is positioned between the first internal space 270 and the second internal space 271. A first internal partition 273 is formed between the first internal space 270 and the second internal space 271, a second internal partition 274 is formed between the second internal space 271 and the third internal space 272, and a third internal partition 275 is formed between the second internal space 272 and the first internal space 270. A first internal hole 276 is formed through the third internal partition 275 and a second internal hole 277 is formed through the second internal partition 274.

The filter 260 is disposed in the first internal space 270 and filters out gas flowing into the first internal space 270 through the second guide hole 230a. The gas filtered out by the filter 260 moves into the third space 272 through the first internal hole 276. The door member 280 is provided to adjust the opening area of the first internal hole 276.

The door member 280 has a rotary shaft 282 mounted on a first side of the third internal partition 275, a rotary plate 284 formed in a plate shape to cover the first internal hole 276, having the rotary shaft 282 inserted in the center thereof, and having an opening hole 284 at a first side, and a knob 286 having a first side connected to the rotary shaft 282 and a second side disposed outside the main body 210 through the main body 210. The knob 286 is formed to be easily held and rotated by a user. The opening hole 284a is moved to face or not to face the first internal hole 276 by rotation of the knob 286, whereby the first internal hole 276 is opened or closed. That is, when the rotary plate 284 is rotated by rotation of the knob 286 and a first side of the rotary plate 284 where the opening hole 284a is formed is positioned to face the first internal hole 276, the first internal hole 276 is opened by the opening hole 284a. On the contrary, when a second side of the rotary plate 284 where the opening hole 284a is not formed is positioned to face the first internal hole 276, the first internal hole 276 is closed by the second side of the rotary plate 284.

The opening hole 284a is formed in an arch shape along the rotational circumference of the rotary plate 284. The opening hole 284a increases in width from a first side to a second side. The first side of the opening hole 284a is smaller than the first internal hole 275 and the second side of the opening hole 284a is the same in size as the first internal hole 276. Accordingly, when the first side of the opening hole 284a is positioned to face the first internal hole 276, the size opened to the outside of the first internal hole 276 is smaller than the size of the entire first internal hole 276. However, when the second side of the opening hole 284a is positioned to face the first internal hole 276, the size opened to the outside of the first internal hole 276 is relatively large to corresponding to the size of the entire first internal hole 276. Accordingly, the opening area of the first internal hole 276 is adjusted in accordance with the position of the opening hole 284a facing the first internal hole 276.

Hereafter, the operation of the smoke evacuation device with fluid storage for laparoscopic surgery according to the second embodiment of the present invention is described.

Figure 10:
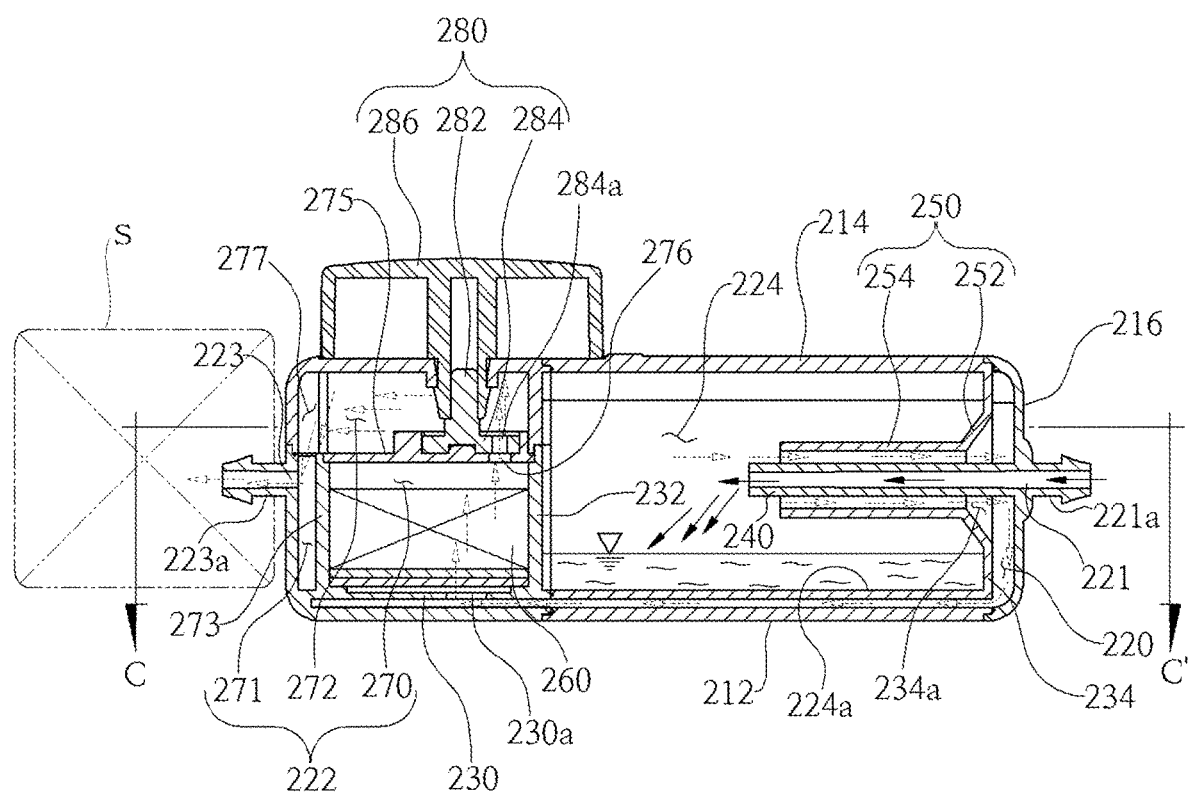
FIG. 10 is a view schematically showing the flowing path of fluid that flows into the smoke evacuation device with fluid storage for laparoscopic surgery according to the second embodiment of the present invention.
Figure 11:
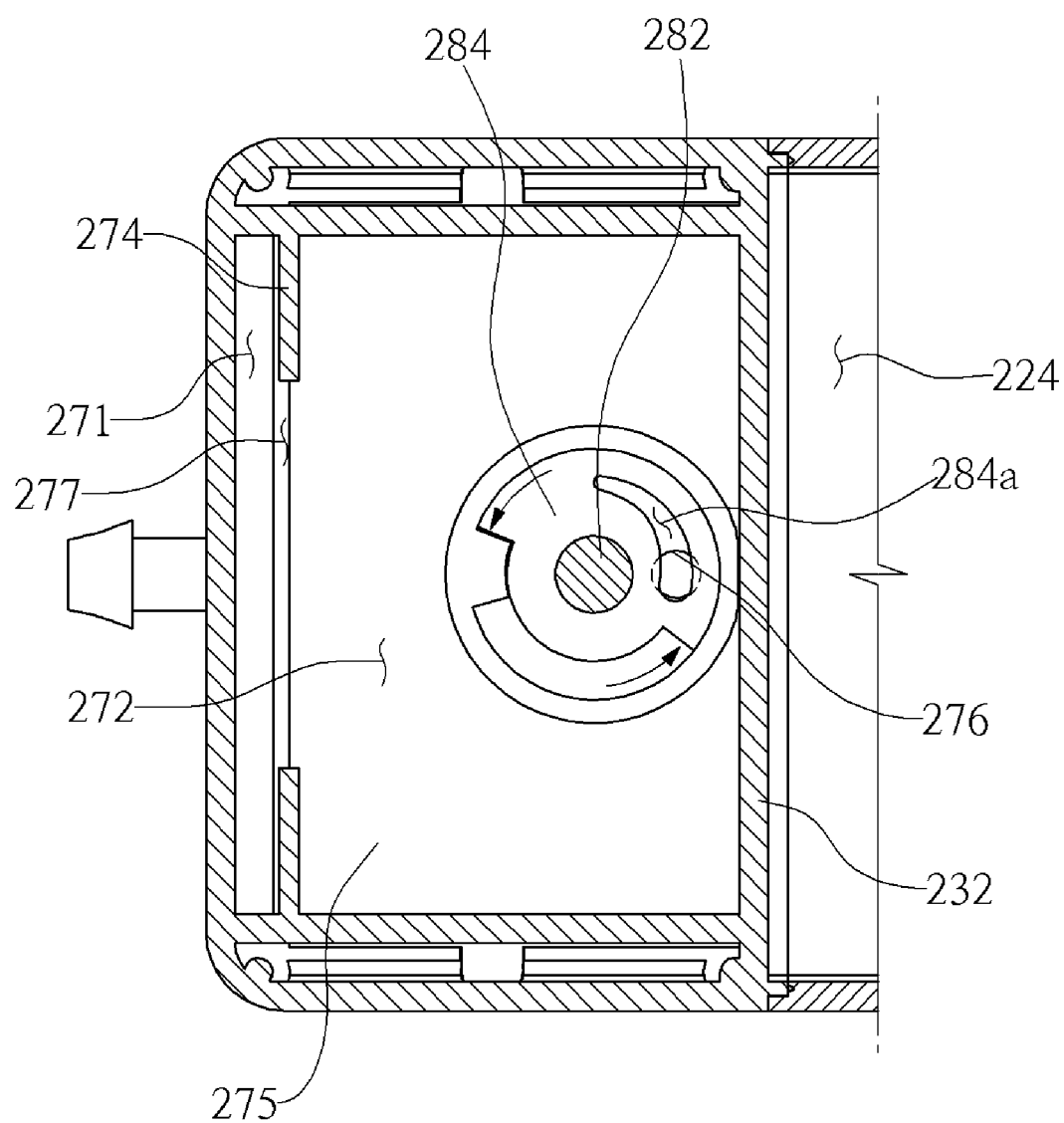
FIG. 11 is a cross-sectional view taken along line C-C' of FIG. 10.

FIG. 10 is a view schematically showing the flowing path of fluid that flows into the smoke evacuation device with fluid storage for laparoscopic surgery according to the second embodiment of the present invention and FIG. 11 is a cross-sectional view taken along line C-C' of FIG. 10.

Referring to FIGS. 10 to 11, the exhaust part (not shown) of a laparoscopic trocar and the connecting protrusion 221*a* are connected to each other by a connecting tube (not shown). In this state, a user rotates the door member 280 to open the first internal hole 276 to the third internal space 272.

Then, fluid flowing into the intake port 221 through the connecting protrusion 221*a* is guided into the third space 224 through the first guide pipe 240. Moisture contained in the fluid and water produced by condensation due to a temperature difference are kept in the third space 224. Gas moving into the third space 224 moves through the space between the first guide pipe 240 and the second guide pipe 250 and is then guided into the first space 220 through the first guide hole 234*a*. The gas of the fluid guided into the first space 220 moves to the first internal space 270 through the second guide hole 230*a*. The gas moving into the first internal space 270 through the second guide hole 230*a* is filtered out by the filter 260 and then moves to the third internal space 272 through the first internal hole 276. The gas moving into the third space 272 moves to the second internal space 271 through the second internal hole 277. The gas moving into the second internal space 271 is finally discharged to the discharge port 223. The discharge port 223 has a discharge protrusion 223*a* and a suction device S that suctions gas is disposed at the discharge protrusion 223*a*, so the gas discharged to the discharge port 223 from the second internal space 271 is automatically discharged by the suction device S.

Although the present invention was described above with reference to the embodiment, the present invention is not limited to the embodiment and it is apparent to those skilled in the art that the present invention may be changed and modified in various ways within the scope of the present invention. Further, the changes and modifications should be construed as being included in the present invention if they belong to the claims.

What is claimed is:

1. A smoke evacuation device with fluid storage for laparoscopic surgery that coupled to an exhaust part of a laparoscopic trocar that is inserted into a human body in laparoscopic surgery, the smoke evacuation device comprising:
    a main body having an empty space and having an intake port formed through a first side thereof to be connected with the exhaust part and a discharge port formed through a second side; and
    a filter disposed at a first side in the main body,
    wherein a first guide pipe through which fluid flowing into the intake port flows to a second side in the main body and a second guide pipe formed along an outer surface of the first guide pipe are disposed in the main body, and when fluid is guided into the main body by the first guide pipe, moisture in the fluid is kept in the main body and gas in the fluid moves toward the filter through a space between the first guide pipe and the second guide pipe, is filtered out, and is then discharged through the discharge port, and
    wherein the space in the main body includes a first space that communicates with the intake port, a second space that is disposed at a first side of the first space to communicate with the discharge port and in which the filter is disposed, a third space that is positioned between a second side of the first space and the second space, a second guide hole is formed at the first side of the first space toward the second space, and a first guide hole is formed at the second side of the first space toward the third space;
    the first guide pipe has a first side connected to the intake port and a second side extending through the first guide hole to be positioned in the third space and has a diameter smaller than the first guide hole; and
    the second guide pipe has a first side connected to an inner edge of the first guide hole and a second side extending along the outer surface of the first guide pipe to be positioned in the third space.

2. The smoke evacuation device with fluid storage of claim 1, wherein a first partition is formed between the first side of the first space and the second space, a second partition is formed between the second space and the third space, and a third partition is formed between the third space and the first space;
    the second guide hole is formed through the first partition, and the first guide hole is formed through the third partition; and
    fluid guided into the third space through the intake port and the first guide pipe from the exhaust part of the laparoscopic trocar moves through a space between the first guide pipe and the second guide pipe and is then guided into the first space through the first guide pipe, the fluid guided into the first space moves into the second space through the second guide hole, and gas of the fluid guided into the second space is filtered out by the filter disposed in the second space and is then discharged through the discharge port.

3. The smoke evacuation device with fluid storage of claim 1, wherein the second guide pipe comprises:
    funnel portion connected to the inner edge of the first guide hole and protruding from the first guide hole such that a width thereof decreases as it goes away from the first guide hole; and
    an outer extension extending from an end of the funnel portion toward an end of the second guide pipe.

4. The smoke evacuation device with fluid storage of claim 1, wherein an end of the first guide pipe protrudes further than an end of the second guide pipe.

5. The smoke evacuation device with fluid storage of claim 1, wherein an end of the first guide pipe and an end of the second guide pipe are not in contact with an inner side of the third space.

6. The smoke evacuation device with fluid storage of claim 5, wherein the first guide pipe and the second guide pipe are spaced apart from a bottom side, which faces the ground, of the inner side of the third space.

7. The smoke evacuation device with fluid storage of claim 6, wherein the first guide pipe and the second guide pipe are in parallel with the bottom side.

8. The smoke evacuation device with fluid storage of claim 6, wherein the intake port is disposed higher than the first guide hole, and
    the first guide pipe has an inclined portion having a first side connected to the intake port and a second side inclined downward toward the first guide hole, and an inner extension extending from the second side of the inclined portion and spaced apart from the bottom side.

9. The smoke evacuation device with fluid storage of claim 8, wherein a diameter of the inclined portion increases from the first side thereof positioned at the intake port to the second side thereof positioned at the first guide hole.

10. The smoke evacuation device with fluid storage of claim 1, further comprising a door member adjusting an opening area of the discharge port.

11. The smoke evacuation device with fluid storage of claim 10, wherein an edge part protrudes outward from the main body along an inner edge of the discharge part;
- an inner edge of the edge part has a first inner edge, a second inner edge, and a third inner edge sequentially positioned away from the second space;
- a blocking portion is formed to close a first side of the first inner edge and an opening portion is formed to open a second side of the first edge;
- a pair of guide rails is formed at both sides in a longitudinal direction of the second inner edge, the blocking portion is positioned between first sides of the pair of guide rails, and the opening portion is positioned between second sides of the pair or guide rails;
- a cover portion is formed to cover the third inner edge, a slit is formed in a longitudinal direction of the cover portion, a first side of the slit is positioned to face the blocking portion, and a second side of the slit is positioned to face the opening portion;
- a first side of the door member has an area being able to close the opening portion and can slide along the guide rails, and a second side of the door member protrudes out of the edge part through the slit; and
- when the second side of the door member slides along the slit, the first side of the door member adjusts an opening area of the opening portion while moving along the guide rail.

12. The smoke evacuation device with fluid storage of claim 11, wherein a cover plate is formed to cover an inner edge of the discharge port; a through-hole is formed through a first side, which faces the blocking portion, of the cover plate; the first side of the cover plate which faces the blocking portion is positioned away from the second guide hole further than a second side of the cover plate; and a first side of the filter is positioned to cover the second guide hole and a second side of the filter is positioned to face the through-hole.

13. The smoke evacuation device with fluid storage of claim 1, wherein the intake port and the first guide hole are positioned to face each other and the first guide hole has a larger diameter than the intake port.

14. The smoke evacuation device with fluid storage of claim 1, wherein the second space includes a first internal space that communicates with the second guide hole, a second internal space that communicates with the discharge port, and a third internal space that is positioned between the first internal space and the second internal space, in which a first internal partition is formed between the first internal space and the second internal space, a second internal partition is formed between the second internal space and the third internal space, and a third internal partition is formed between the second internal space and the first internal space;
- a first internal hole is formed through the third internal partition and a second internal hole is formed through the second internal partition;
- the filter is disposed in the first internal space;
- the smoke evacuation device with fluid storage further includes a door member adjusting an opening area of the first internal hole; and
- gas of fluid moving into the first internal space through the second guide hole is filtered out by the filter and then moves into the third internal space through the first internal hole, the gas moving into the third internal space moves into the second internal space through the second internal hole, and the gas moving into the second internal space is discharged to the discharge port.

15. The smoke evacuation device with fluid storage of claim 14, wherein the door member has a rotary shaft mounted on a first side of the third internal partition, a rotary plate formed in a plate shape to cover the first internal hole, having the rotary shaft inserted in a center thereof, and having an opening hole at a first side, and a knob having a first side connected to the rotary shaft and a second side disposed outside the main body through the main body; and
- the opening hole is moved to face or not to face the first internal hole by rotation of the knob, whereby the first internal hole is opened or closed.

16. The smoke evacuation device with fluid storage of claim 15, wherein the opening hole is formed in an arch shape along a rotational circumference of the rotary plate such that a width increases from a first side to a second side; and
- a size opened to the outside of the first internal hole when the first side of the opening hole is positioned to face the first internal hole is larger than a size opened to the outside of the first internal hole when the second side of the opening hole is positioned to face the first internal hole.

17. A smoke evacuation device with fluid storage for laparoscopic surgery that coupled to an exhaust part of a laparoscopic trocar that is inserted into a human body in laparoscopic surgery, the smoke evacuation device comprising:
- a main body having an empty space and having an intake port formed through a first side thereof to be connected with the exhaust part and a discharge port formed through a second side; and
- a filter disposed at a first side in the main body,
- wherein a first guide pipe through which fluid flowing into the intake port flows to a second side in the main body and a second guide pipe formed along an outer surface of the first guide pipe are disposed in the main body, and when fluid is guided into the main body by the first guide pipe, moisture in the fluid is kept in the main body and gas in the fluid moves toward the filter through a space between the first guide pipe and the second guide pipe, is filtered out, and is then discharged through the discharge port, and
- wherein the discharge port is positioned at an upper portion of the main body and the intake port is positioned lower than the discharge port, so fluid guided into the main body through the intake port is manually discharged to the discharge port.

18. A smoke evacuation device with fluid storage for laparoscopic surgery that coupled to an exhaust part of a laparoscopic trocar that is inserted into a human body in laparoscopic surgery, the smoke evacuation device comprising:
- a main body having an empty space and having an intake port formed through a first side thereof to be connected with the exhaust part and a discharge port formed through a second side; and
- a filter disposed at a first side in the main body,
- wherein a first guide pipe through which fluid flowing into the intake port flows to a second side in the main body and a second guide pipe formed along an outer surface of the first guide pipe are disposed in the main body, and when fluid is guided into the main body by the first guide pipe, moisture in the fluid is kept in the main body and gas in the fluid moves toward the filter through a space between the first guide pipe and the second guide pipe, is filtered out, and is then discharged through the discharge port, and wherein fluid discharged to the discharge port from the inside of the main body is automatically discharged by a suction device disposed at the discharge port and suctioning fluid.

* * * * *